| United States Patent [19] | | [11] | 4,028,361 |
|---|---|---|---|
| Sayigh et al. | | [45] | June 7, 1977 |

[54] PROCESS FOR THE PURIFICATION OF MDA

[75] Inventors: Adnan A. R. Sayigh, North Haven; Kwok K. Sun, Hamden; Henri Ulrich, Northford, all of Conn.

[73] Assignee: The Upjohn Company, Kalamazoo, Mich.

[22] Filed: Aug. 18, 1975

[21] Appl. No.: 605,751

[52] U.S. Cl. .................... 260/570 D; 260/248 NS; 260/570.5 P
[51] Int. Cl.$^2$ ......................... C07C 85/16
[58] Field of Search ............................ 260/570 D

[56] References Cited

UNITED STATES PATENTS

| 3,676,497 | 7/1972 | Recchia et al. | 260/570 |
| 3,857,890 | 12/1974 | Recchia et al. | 260/570 |
| 3,860,637 | 1/1975 | Bentley | 260/570 |

FOREIGN PATENTS OR APPLICATIONS

| 863,983 | 2/1971 | Canada | 260/570 |
| 1,127,347 | 9/1968 | United Kingdom | 260/570 |
| 1,292,078 | 10/1972 | United Kingdom | 260/570 |

OTHER PUBLICATIONS

Allied Chemical, "Aniline," p. 35 (1964).

*Primary Examiner*—Robert V. Hines
*Attorney, Agent, or Firm*—Denis A. Firth; John Kekich

[57] ABSTRACT

A process is described for the selective removal of 2,2'- and 2,4'-diaminodiphenylmethane from mixtures thereof with the corresponding 4,4'-isomer by heating the mixture of isomers in the presence of a 1,3,5-triarylhexahydro-1,3,5-triazine and a catalyst (aqueous mineral acid). The process is particularly useful in facilitating the isolation of substantially pure 4,4'-isomer from the aniline-formaldehyde condensation. The pure 4,4'-isomer is a valuable intermediate for polyamides as well as for the corresponding diisocyanate. The by-products of the reaction are oligomeric polymethylene polyphenyl polyamines which are also useful as curing agents and intermediates for polymethylene polyphenyl polyisocyanates and the like.

12 Claims, No Drawings

PROCESS FOR THE PURIFICATION OF MDA

BACKGROUND OF THE INVENTION

1. Field of the Invention

This invention relates to the preparation of diamines and is more particularly concerned with the selective removal of 2,2'and 2,4'-diaminodiphenylmethane from mixtures with 4,4'-diaminodiphenylmethane.

2. Description of the Prior Art

The condensation of aniline with formaldehyde in the presence of catalysts such as mineral acids, siliceous materials and the like, is well-known in the art; see, for example, U.S. Pat. Nos. 2,638,730; 2,950,263; 3,260,751; 3,277,173; 3,297,759; 3,362,979; and 3,476,806. The principal component of the product of this condensation is di(aminophenyl)methane the remaining components being oligomeric methylene polyphenyl polyamines, e.g., triamines, tetramines, etc. The proportion of diamine present in the mixture depends to a large extent on the molar proportion of aniline to formaldehyde. In general, the higher the proportion of aniline to formaldehyde, the higher the proportion of diamine in the product. The majority of the diamine is obtained as the 4,4'-isomer, the 2,4'-isomer being present in relatively minor proportion together with very small amounts of the 2,2'-isomer. The proportion of the isomers in any given product is dependent upon the reactant proportions and conditions employed in the reaction.

To date, no process has been devised which will give a product containing diamine which is exclusively in the form of the 4,4'-isomer. Proportions of 4,4'-isomer as high as 98 percent and as low as 40 percent or less have been reported. However, for many purposes, particularly where the diamine is to be used as an intermediate in the preparation of linear polyamides, polymides, and similar polymers, it is desirable, if not essential, that the diamine be substantially pure 4,4'-isomer, i.e., that the content of 2,2'- and/or 2,4'-isomer be only 2 percent by weight or less. Accordingly, the diamine isolated from the aniline-formaldehyde condensation (or the corresponding diisocyanate obtained by phosgenation of the diamine alone or as part of the mixture of polyamines obtained in the condensation) has been purified by conventional techniques such as fractional distillation, fractional crystallization, and the like, to achieve the desired purity of the 4,4'-isomer. Not only are such techniques tedious and expensive to operate on a commercial scale, but they produce, as by-product, the 2,4'-isomer, or fractions enriched in 2,4'-isomer, which are of much less utility than the 4,4'-isomer.

We have now found that the 2,2'- and 2,4'-diaminodiphenylmethanes can be selectively removed from a mixture of said isomers with 4,4'-diaminodiphenylmethane by a process which will be described below. This process can be applied successfully to relatively pure mixtures of 2,2'-, 2,4'- and 4,4'-diaminodiphenylmethane as well as to mixtures of these diamines oligomeric polyamines obtained in the condensation of aniline with formaldehyde.

SUMMARY OF THE INVENTION

The invention comprises a process for selectively removing 2,2'- and 2,4'-diaminodiphenylmethanes from admixtures thereof with 4,4'-diaminodiphenylmethane which process comprises heating said mixtures with a member selected from the class consisting of 1,3,5-triarylhexahydro-1,3,5-triazines and polyaminals obtained as by-product in the formation of said triazines, at a temperature of about 30° C to about 100° C in the presence of aqueous mineral acid.

The mixtures of 2,2'-, 2,4'- and 4,4'-diaminodiphenylmethane employed in the above process can be substantially pure, i.e., free from oligomeric polyamines or the mixtures of isomers can be present in admixture with oligomeric polyamines as in the case of the mixtures isolated from the reaction product of aniline and formaldehyde under conditions well-known in the art (supra).

The term "1,3,5-triarylhexahydro-1,3,5-triazine" means a compound of the formula:

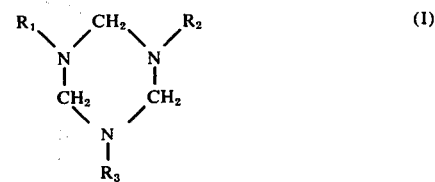

wherein $R_1$, $R_2$, and $R_3$ are independently selected from the class consisting of phenyl and phenyl substituted by one or more (up to five) electron-donating substituents. The latter are a well-known class of substituents in aromatic rings and are inclusive of alkyl from 1 to 6 carbon atoms, inclusive, such as methyl, ethyl, propyl, butyl, pentyl, hexyl and isomeric forms thereof; alkoxy from 1 to 6 carbon atoms, inclusive, such as methoxy, ethoxy, propoxy, butoxy, pentoxy, hexyloxy and isomeric forms thereof; amino; dialkylamino, wherein each alkyl is as above defined; and halogen, i.e., chloro, bromo, and iodo.

The "polyaminals" employed in the process of the invention are the higher molecular weight, cyclic and/or linear polymers formed as the by-product of reaction of the arylamine and formaldehyde employed in the preparation of the hexahydro-1,3,5-triazines (I). The cyclic polyaminals formed as by-product of the reaction of paraformaldehyde and the amine $R_1NH_2$, wherein $R_1$ has the meaning defined above, can be represented by the formula $(R_1NCH_2)_x$ where $x$ is an integer from about 3 up to about 10. The linear polyaminals formed as by-products of the same reaction can be represented as

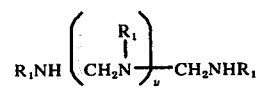

wherein $R_1$ has the above meaning and $y$ is an integer from 0 to about 10.

DETAILED DESCRIPTION OF THE INVENTION

The process of the invention is carried out conveniently by bringing the reactants together, in any order, and heating the resulting mixtures at a temperature within the range of about 30° to about 100 ° C until routine analytical procedures, carried out on an aliquot, indicate that removal of the 2,2'- and 2,4'-isomers of the diamine has proceeded to the required extent. Advantageously, the mixture of amines is first dissolved in the aqueous mineral acid solution and the hexahydrotriazine (I) or polyaminal is added thereto, preferably with stirring.

The aqueous mineral acids employed in the process of the invention are inclusive of hydrochloric, hydrobromic, sulfuric and phosphoric acids. The preferred acid is aqueous hydrochloric acid.

The aqueous mineral acid employed in the reaction mixture advantageously has an initial concentration within the range of about 0.1N to about 5.0N and preferably within the range of about 1.0N to about 2.0N. The amount of mineral acid employed in the process of the invention is such that, for each equivalent of amine in the starting amine mixture, there is employed from about 0.55 to about 0.95 equivalents of acid. When the mixture of isomeric diamines employed as starting material is present in admixture with oligomeric methylene polyphenyl polyamines, the amine equivalents of the latter are included in calculating the amount of mineral acid to be employed.

The proportion of hexahydrotriazine (I) or polyaminal which is employed in the process of the invention varies according to the amount of 2,2'- and 2,4'-isomers of the diamine present in the starting material. Advantageously, the proportion of hexahydrotriazine (I) or polyaminal is from about 0.1 equivalent to about 1.5 equivalents per mole of the total of 2,2'- and 2,4'-diaminodiphenylmethane present in the starting material. Preferably, the proportion of hexahydrotriazine (I) or polyaminal is from about 0.2 equivalent to about 0.9 equivalent per mole of the total of 2,2'- and 2,4'-diaminodiphenylmethane present in the starting material. The term "equivalent" is used in its conventional sense in regard to the hexahydrotriazine (I) or the polyaminals, i.e., the equivalent weight of the materials in question is the molecular weight divided by the number of nitrogen atoms per molecule.

The mixture of isomeric diamines, aqueous mineral acid and hexahydrotriazine (I) or polyanimals is heated at a temperature in the above range, advantageously with stirring, until the reacton is complete or has reached any desired stage. The progress of the reaction can be followed by routine analytical techniques performed on aliquots. Such techniques include gas liquid phase chromatography, thin layer chromatography and the like. When the reaction has reached the desired stage, the diamines, and oligomeric polyamines are isolated from the reaction mixture by neutralizing the acid in the reaction mixture, using a base such as sodium hydroxide, and extracting the liberated amines using an appropriate organic solvent such as chloroform, methylene chloride, benzene, toluene, chlorobenzene, dichlorobenzene, ethyl acetate, and the like. If so desired, the 4,4'-diaminodiphenylmethane can be isolated in substantially pure form from the reaction product by fractional distillation, fractional crystallization and like techniques.

The by-products produced by conversion of the 2,2'- and 2,4'-isomers of the diamine in accordance with the process of the invention are oligomeric methylene polyphenyl polyamines. Such products are themselves useful, illustratively, as curatives for epoxy resins and as intermediates in that they can be phosgenated to form the corresponding polymethylene polyphenyl polyisocyanates. Indeed, in a particular embodiment of the process of the invention the total amine product from the process, i.e., the mixture of 4,4'-diaminodiphenylmethane and oligomeric methylene polyphenyl polyamines, is isolated as such and phosgenated, using conventional procedures, to the corresponding mixture of 4,4'-diisocyanatodiphenylmethane and oligomeric polymethylene polyphenyl polyisocyanates. The mixture is useful as such in the preparation of rigid polyurethane and polyisocyanurate foams and in the preparation of adhesives, rigid noncellular plastics and the like using techniques well-known in the art. Alternatively, the mixture can be subjected to fractional distillation using thin film evaporators, using techniques such as those described in U.S. Pat. No. 3,471,543, to isolate substantially pure 4,4'-diisocyanatodiphenylmethane. The latter is useful as an intermediate in the preparation of linear polyurethane elastomers using techniques well-known in the art. As set forth above, the process of the invention can be applied to selectively remove 2,2'- and 2,4'-diaminodiphenylmethane contained in admixture with the 4,4'-isomer and/or with oligomeric methylene polyphenyl polyamines. In a particular embodiment the process of the invention is applied to a mixture of 2,2'-, 2,4'- and 4,4'-diaminodiphenylmethanes which has been isolated as the forecut in the fractional distillation of 4,4'-diaminodiphenylmethane containing minor amounts of the 2,2'- and 2,4'-isomers, the latter having been isolated from the reaction product of aniline and formaldehyde using processes commercially employed in the art.

While any of the hexahydrotriazines (I) can be employed in the process of the invention, it is preferred to use 1,3,5-triphenylhexahydro-1,3,5-triazine [I; $R_1 = R_2 = R_3$ = phenyl]. Thus if one uses a hexahydro triazine (I) in which one or more of $R_1$, $R_2$, and $R_3$ is a substituted phenyl it is found that, at least in some cases, the 4,4'-diaminodiphenylmethane becomes contaminated with small proportions of mixed diamine in which one of the 4-aminophenyl rings of the diamine is replaced by the substituted phenyl ring derived from the hexahydrotriazine. The mixed diamine can, of course, be separated from the desired 4,4'-diaminophenylmethane by conventional techniques such as fractional distillation.

The hexahydrotriazines (I) and polyaminals which are employed in the process of the invention are prepared by procedures well-known in the art; for example, they are prepared by reaction of paraformaldehyde with the appropriate amine under the conditions described by M. Wakae et al., Osaka Furitsu Kogyo-Shoreikan Hokoku, No. 29, 47, 1963 (Chemical Abstracts 59, 6280g, 1963).

The following examples describe the manner and process of making and using the invention and set forth the best mode contemplated by the inventors of carrying out the invention but are not to be construed as limiting.

EXAMPLE 1

A mixture of 1.0 g. 5.5 mmol.) of diaminodiphenylmethane (contaning equal parts by weight of 2,4'- and 4,4'-isomer) and 9.0 ml. (9 mmol.) of N aqueous hydrochloric acid was heated at 100° C in an oil bath with stirring and 0.21 g. (0.66 mmol.) of 1,3,5-triphenylhexahydro-1,3,5-triazine was added. The mixture was stirred for 0.5 hr. at the same temperature an then a second portion of 0.21 g. (0.66 mmol.) of the same hexahydrotriazine together with 4 ml. (4 mmol.) of N aqueous hydrochloric acid was added. The mixture was again stirred at 100° C for 0.5 hr. and a final portion of 0.053 g. (0.166 mmol.) of the same hexahydrotriazine was added together with 0.5 ml. (0.5 mmol.) of N aqueous hydrochloric acid. The resulting mixture was stirred at 100° C for a further hour. The final product was cooled to room temperature (circa 20° C) and neutralized by the addition of 5N aqueous sodium hydroxide. The liberated amine was extracted with chloroform and the chloroform extract was washed with water, dried over anhydrous sodium sulfate and evaporated to dryness. The residue was found by gas liquid phase chromatography (glpc), using 2,2-di(4-aminophenyl) propane as internal standard, to contain 2.46 mmol. (48.8 percent yield) of diaminodiphenylmethane and the latter was found to contain 98.1 percent of 4,4'-isomer and only 1.9 percent of 2,4'-isomer.

EXAMPLE 2 a. A mixture of 3 g. (15.15 mmol.) of diaminodiphenylmethane (containing 15 percent by weight of 2,4'-isomer and 85 percent by weight of 4,4'-isomer) and 27 ml. (27 mmol.) of N aqueous hydrochloric acid was stirred and heated at 95° to 100° C and an initial portion (0.315 g; 1 mmol.) of 1,3,5-triphenylhexahydro-1,3,5-triazine was added. The resulting mixture was heated at 95° to 100° C for 0.5 hr. whereupon a second portion (0.158 g.; 0.5 mmol.) of the same hexahydrotriazine was added. Heating was continued for a further 0.5 hr. at 95° to 100° C after which a third portion (0.158 g.; 0.5 mmol.) of the same hexahydrotriazine was added. The mixture was then heated for a further 0.5 hr. at the same temperature before being cooled to room temperature (circa 20° C). The mixture was worked-up as described in Example 1. The product was subjected to glpc analysis using 2,2'-diaminodiphenylmethane as internal standard and was found to contain 11.8 mmol. (78.5 percent yield) of diaminodiphenylmethanes of which 98.2 percent by weight was 4,4'-isomer and 1.8 percent by weight was 2,4'-isomer.

b. A mixture of 1.0 g. (5.05 mmol.) of diaminodiphenylmethane (containing 15 percent by weight of 2,4'-isomer and 85 percent by weight of 4,4'-isomer), 9 ml. (9.0 mmol.) of N aqueous hydrochloric acid solution and 0.105 g. (0.33 mmol.) of 1,3,5-triphenylhexahydro-1,3,5-triazine was stirred and heated at 95° to 100° C for 2 hr. At the end of this period the mixture was worked-up as described in Example 1. The product was subjected to glpc analysis and was found to contain 3.60 mmol. (71.5 percent yield) of diaminodiphenylmethanes of which 95.7 percent weight was the 4,4'-isomer and 4.3 percent by weight was the 2,4'-isomer.

EXAMPLE 3

This example shows the preparation of 1,3,5-triphenylhexahydro-1,3,5-triazine and certain polyaminals and the use of these polyaminals in the selective removal of 2,4'- and 2,2'-diaminodiphenylmethane from admixture with the corresponding 4,4'-isomer.

a. A mixture of 40 g. (1.33 mole) of paraformaldehyde, 100 g. (1.07 mole) of aniline, 200 ml. of methanol and 10 g. of sodium acetate was heated under reflux for 2.5 hr. and then allowed to stand overnight. The resulting mixture was filtered and the solid so isolated was extracted with hot benzene from which extract there separated 53.8 g. of 1,3,5-triphenyl-1,3,5-hexahydrotriazine as a crystalline solid of melting point 141° to 143° C which was isolated by filtration. The original solid which had not dissolved in the hot benzene extract was further extracted with chloroform and the chloroform was evaporated to dryness to give 12.8 g. of crystalline material (polyaminal) having a melting point 255°–259° C. This material is referred to hereafter as

POLYAMINAL A

The filtrate from the filtration of the original reaction mixture was found to have separated into two layers. The lower (organic) layer (49 g.) was separated, filtered to remove a small proportion of solid sediment and the filtrate was treated with isopropanol. The solid which separated was isolated by filtration and washed with carbon tetrachloride. The residual white solid (6.8 g.) was a second fraction of polyaminal [hereinafter Polyaminal B] having a melting point of 194° to 199° C.

b. A mixture of 1.0 g. (5.05 mmol.) of diaminodiphenylmethane (containing 15 percent by weight of 2,4'-isomer and 85 percent by weight of 4,4'-isomer) and 9.0 ml. (9.0 mmol.) of N aqueous hydrochloric acid was stirred and heated at 95° to 100° C and 2.1 g. (2 milliequiv.) of Polyaminal A was added. The mixture was heated at the above temperature with stirring for 6 hr. at the end of which time the mixture was cooled to room temperature. An aliquot was neutralized by 5N aqueous sodium hydroxide and the diaminodiphenylmethane thus liberated was found by glpc. to contain 98.4 percent by weight of the 4,4'-isomer and 1.6 percent by weight of the 2,4'-isomer.

c. The procedure described in part (b) above was repeated but replacing Polyaminal A by an equivalent amount of Polyaminal B. There was thus obtained diaminodiphenylmethane of whicch 97.6 percent by weight was 4,4'-isomer and 2.4 percent by weight was 2,4'-isomer.

We claim:
1. A process for selectively removing 2,2'- and 2,4'-diaminodiphenylmethanes from admixtures thereof with 4,4'-diaminodiphenylmethane which comprises heating said mixtures of isomeric diamines with a member selected from the class consisting of 1,3,5-triarylhexahydro-1,3,5-triazines and polyaminals obtained as by-products in the formation of said triazines, said heating being carried out at a temperature of about 30° C to about 100° C in the presence of aqueous mineral acid.

2. The process of claim 1 wherein the mineral acid is hydrochloric acid.

3. The process of claim 1 wherein the proportion of 1,3,5-triarylhexahydro-1,3,5-triazine or polyaminal is within the range of about 0.1 to about 1.5 equivalents per mole of 2,4'-diaminodiphenylmethane.

4. The process of claim 1 wherein the 2,4'-diaminodiphenylmethane employed as starting material is in the form of a mixture of 4,4'-diaminodiphenylmethane and 2,4'-diaminodiphenylmethane which product has been obtained by the condensation of aniline and formaldehyde.

5. The process of claim 1 wherein the 1,3,5-triphenylhexahydro-1,3,5triazine is 1,3,5-triphenylhexahydro-1,3,5-triazine.

6. A process for selectively removing 2,2'- and 2,4'-diaminodiphenylmethanes from admixtures thereof with 4,4'-diaminodiphenylmethane which comprises heating said mixtures with 1,3,5-triphenylhexahydro-1,3,5-triazine in the presence of aqueous hydrochloric acid at a temperature of about 30° c to about 100° c.

7. The process of claim 6 wherein the proportion of 1,3,5-triphenylhexahydro-1,3,5-triphenylhexahydro- 1,3,5-triazine is within the range of about 0.2 to about 0.9 equivalent per mole of diamine.

8. The process of claim 6 wherein the mixture of diamines employed as starting material is in the form of a mixture of 2,2'-, 2,4'- and 4,4'-diaminodiphenylmethanes and oligomeric polyamines which product has been obtained by the condensation of aniline and formaldehyde.

9. The process of claim 6 wherein the aqueous hydrochloric acid is present in an amount representing from about 0.55 to about 0.95 equivalents per equivalent of starting amine and the concentration of said acid is within the range of about 1N to about 2N.

10. A process for selectively removing 2,2'- and 2,4'-diaminodiphenylmethanes from admixtures thereof with 4,4'-diaminodiphenylmethane which comprises heating said mixtures of isomeric diamines with from about 0.2 to 0.9 equivalents, per mole of diamine, of a polyaminal, obtained as by-product in the formation of 1,3,5-triphenylhexahydro-1,3,5-triazine from aniline and paraformaldehyde, said heating being carried out in the presence of aqueous hydrochloric acid at a temperature of about 30° C to about 100° C.

11. The process of claim 10 wherein the mixture of diamines employed as starting material is in the form of a mixture of 2,2'-, 2,4'- and 4,4'-diaminodiphenylmethanes and oligomeric polyamines which product has been obtained by the condensation of aniline and formaldehyde.

12. The process of claim 10 wherein the aqueous hydrochloric acid is present in an amount representing from about 0.55 to about 0.95 equivalents per equivalent of starting amine and the concentration of said acid is within the range of about 1N to about 2N.

* * * * *